(12) United States Patent
Shan et al.

(10) Patent No.: US 10,300,267 B2
(45) Date of Patent: *May 28, 2019

(54) MULTIELECTRODE LEAD WITH MULTIPLEXED CONTROL AND ASSOCIATED CONNECTION METHOD

(71) Applicant: SORIN CRM SAS, Clamart (FR)

(72) Inventors: Nicolas Shan, Juvisy sur Orge (FR); Philippe D'Hiver, Chatillon (FR)

(73) Assignee: Sorin CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/947,753

(22) Filed: Apr. 6, 2018

(65) Prior Publication Data

US 2018/0221650 A1 Aug. 9, 2018

Related U.S. Application Data

(63) Continuation of application No. 15/088,867, filed on Apr. 1, 2016, now Pat. No. 9,937,339.

(51) Int. Cl.
*A61N 1/05* (2006.01)
*A61N 1/02* (2006.01)
(Continued)

(52) U.S. Cl.
CPC .............. *A61N 1/05* (2013.01); *A61N 1/025* (2013.01); *A61N 1/056* (2013.01); *A61N 1/0551* (2013.01);
(Continued)

(58) Field of Classification Search
CPC ........ A61N 1/05; A61N 1/025; A61N 1/0551; A61N 1/056; A61N 1/36125
See application file for complete search history.

(56) References Cited

U.S. PATENT DOCUMENTS

| 8,639,341 B2 | 1/2014 | Sommer et al. |
| 2003/0149456 A1 | 8/2003 | Rottenberg et al. |
| 2011/0301665 A1 | 12/2011 | Mercanzini et al. |

FOREIGN PATENT DOCUMENTS

| EP | 1 938 861 | 7/2008 |
| EP | 2 465 425 | 6/2012 |

(Continued)

OTHER PUBLICATIONS

Preliminary Search Report for French Patent Application No. 1552894, dated Oct. 8, 2015, 2 pages.

*Primary Examiner* — Paula J Stice
(74) *Attorney, Agent, or Firm* — Foley & Lardner LLP

(57) ABSTRACT

The disclosure relates to a lead including a connector for connection to a generator, a demultiplexing circuit receiving at its input on the first conductors of the electrical control signals from the control bus and whose output is connected to a plurality of second conductors contained in the lead and connected to the lead electrodes. The lead further includes a gate and connection circuit component having a body forming a support for an integrated circuit for demultiplexing and defining a set of connection cavities with the second conductor distributed at the periphery of the body around a general axis of the body, and a plurality of connecting elements embedded in the body material, and emerging at an element region and supporting the circuit at respective cavities. The gate and connection circuit component is advantageously made of ceramic-metal.

20 Claims, 4 Drawing Sheets

(51) Int. Cl.
  *A61N 1/36* (2006.01)
  *H01R 24/86* (2011.01)
  *H01R 107/00* (2006.01)

(52) U.S. Cl.
  CPC .. *A61N 1/36125* (2013.01); *A61N 2001/0585* (2013.01); *H01R 24/86* (2013.01); *H01R 2107/00* (2013.01); *H01R 2201/12* (2013.01)

(56) References Cited

FOREIGN PATENT DOCUMENTS

| | | |
|---|---|---|
| EP | 2 727 623 | 5/2014 |
| WO | WO-2004/052182 | 6/2004 |
| WO | WO-2009/018426 | 2/2009 |
| WO | WO-2012/087370 | 6/2012 |

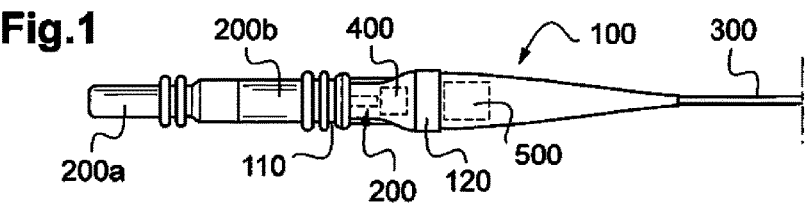
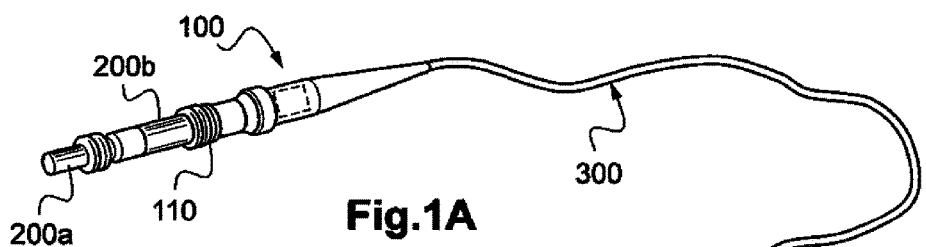
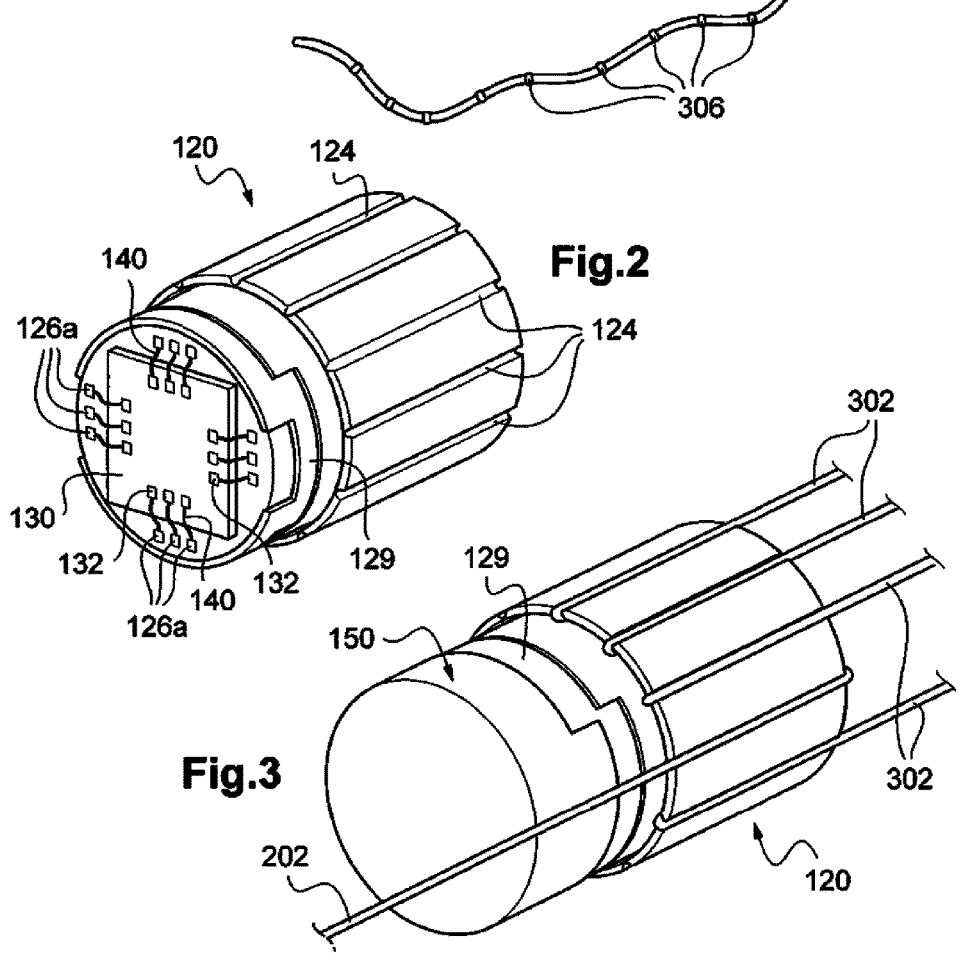

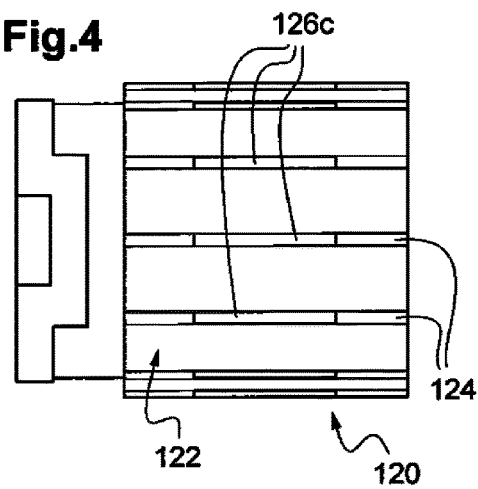
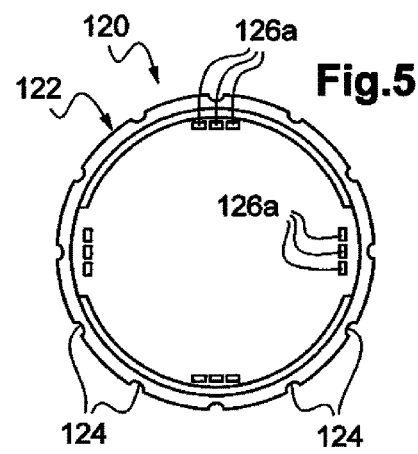
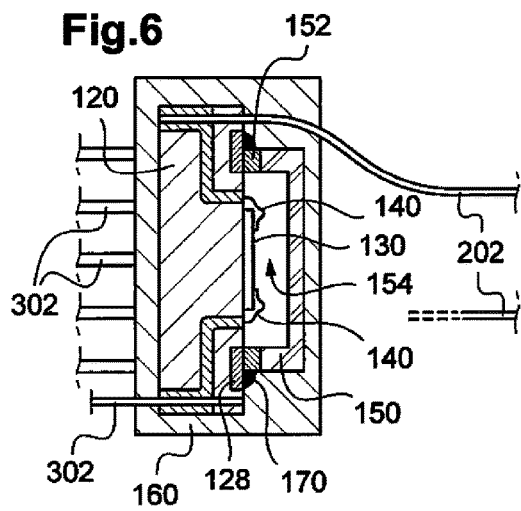
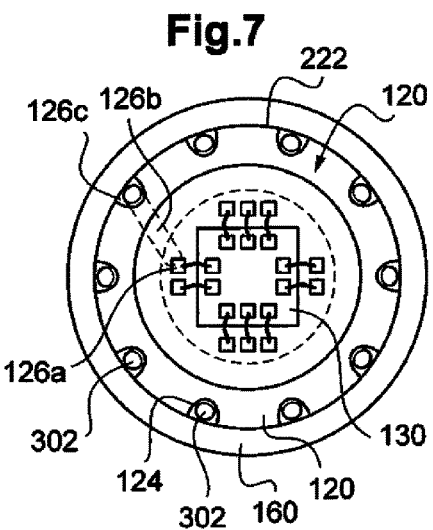
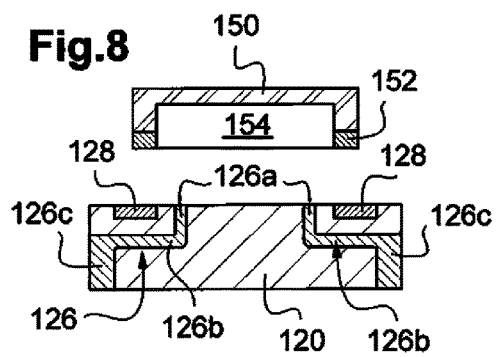
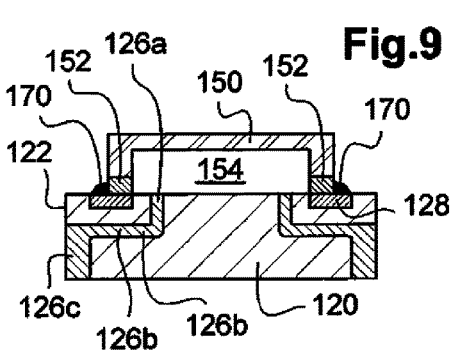

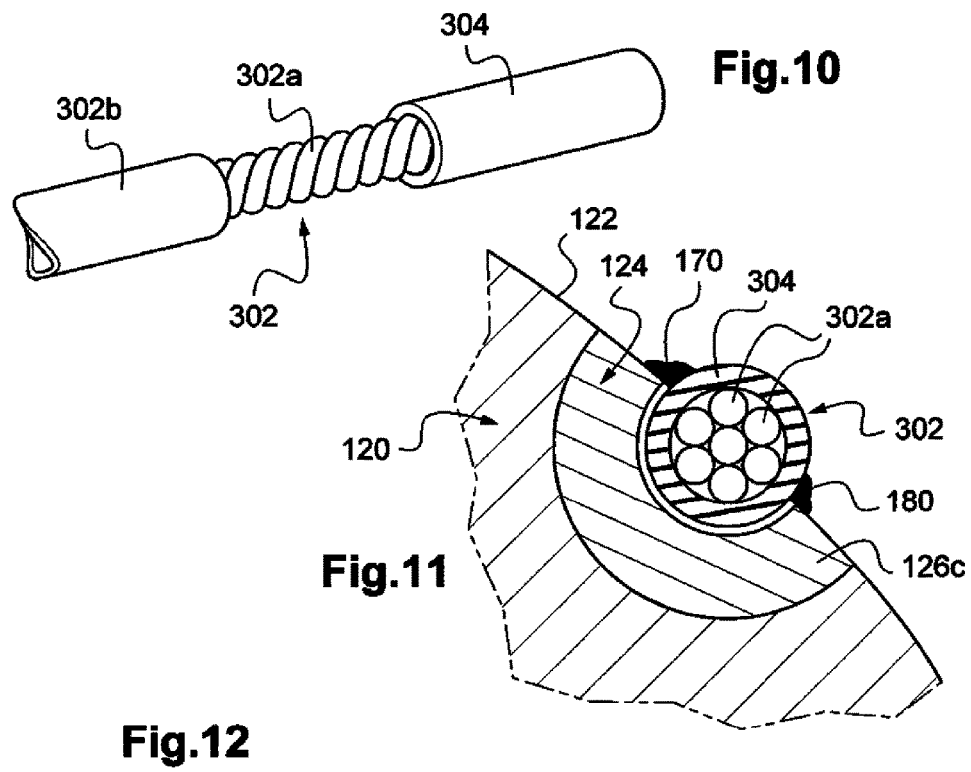
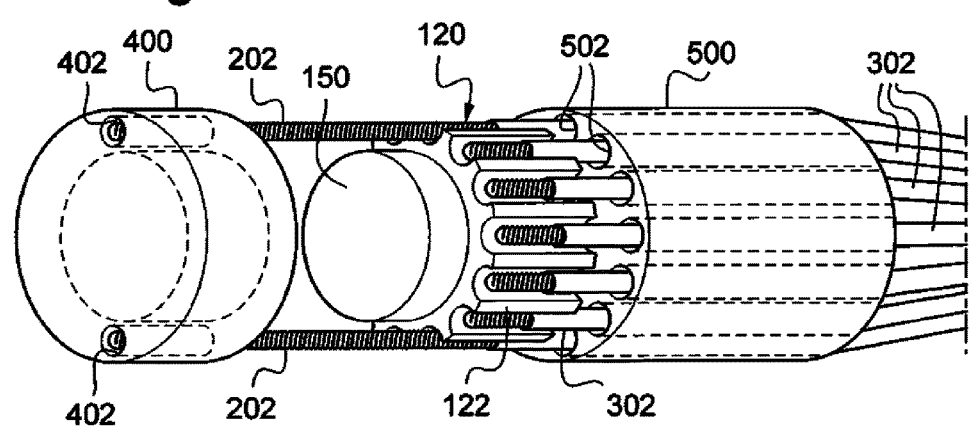
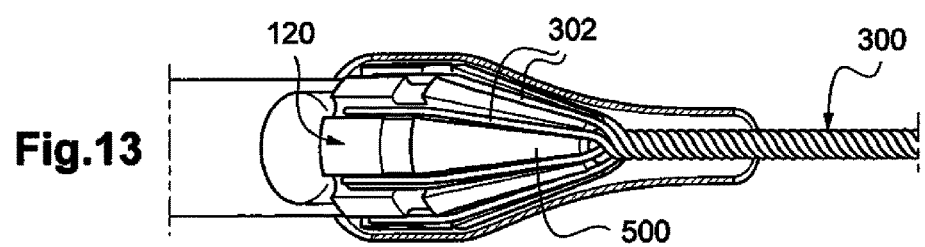

MULTIELECTRODE LEAD WITH MULTIPLEXED CONTROL AND ASSOCIATED CONNECTION METHOD

CROSS-REFERENCE TO RELATED PATENT APPLICATIONS

This application is a continuation of U.S. application Ser. No. 15/088,867, filed Apr. 1, 2016, which claims the benefit of and priority to French Patent Application No. 1552894, filed Apr. 3, 2015, both of which are incorporated herein by reference in their entireties.

BACKGROUND

The disclosure relates to "active implantable medical devices" as defined by the Directive 90/385/EEC of 20 Jun. 1990 by the Council of the European Communities, specifically the "multisite" implants to collect electrical potentials and/or selectively deliver electrical pulses to one or more pacing sites of to a set of sites, particularly in cardiology and neuromodulation applications.

The recent development of such multi-site stimulation devices has led to increasing the number of electrodes, so as to allow the choice of one or more detection/stimulation sites optimizing the operation of the device.

The following disclosure will mainly refer to electrodes used for the application of stimulation pulses, but this feature is not limiting and the disclosure applies equally to the case of electrodes used for detection of electric potentials collected at specific sites, the same electrode possibly being used for both sensing and pacing.

In the particular case of the implantable cardiac devices for ventricular resynchronization or "CRT" (Cardiac Resynchronization Therapy), which are cited here as a non limiting example, a device with electrodes for stimulating one and the other ventricles is implanted in the patient. The stimulation of the right ventricle (and right atrium) is done by a conventional endocardial lead, but for the left ventricle, the access being more complex, the stimulation is generally carried out by a lead inserted into the coronary sinus and then pushed into a coronary vein on the epicardium so that the end of the is positioned in front of the left ventricle.

This procedure is, however, rather difficult, because the diameter of the coronary vessels is reduced with the progress of the lead, so it is not always easy to find the optimum position during implantation. The proximity of the phrenic nerve can also lead to inappropriate stimuli.

To overcome these difficulties, "multielectrode" leads have developed, provided for example with eight or more electrodes, and it is possible to choose, after implantation, the electrode which corresponds to the site on which the stimulation is the most effective. This selection of the electrode can be carried out automatically by a measure of endocardial acceleration peaks (PEA), by a measurement of bioimpedance, or from any other sensor able to provide information representative of the patient's hemodynamic status. It can also be operated manually by the practitioner by a suitable programmer controlling a generator.

These pacing leads must have a diameter as small as possible in order to extend the possibilities of implantation while being the least traumatic for the body.

Furthermore, increasing the number of electrodes creates issues of delicate connection at the connection with the stimulation pulse generator.

The difficulties encountered are similar in neuromodulation applications operating by multipoint stimulation of the central nervous system. Neuromodulation consists, for example, in implanting a microlead in the cerebral venous network in order to achieve very specific target areas of the brain in order to apply electrical stimulation pulses to treat certain conditions such as Parkinson's disease, epilepsy, etc. The purpose can also be to stimulate the peripheral nervous system, the electrodes then being placed at nerves or muscles.

With currently known techniques, increasing the number of electrodes to be connected has a strong impact on the size and cost of internal electronics of the housing, the connector of the housing and the lead, so it may be preferred to use a demultiplexer circuit which makes it possible to decode signals and voltages on a limited number of conductors (typically 2 or 4). It would however be beneficial to be able to increase the number of electrodes while generally reducing the volume of connection between the signal source and the lead, requiring only that these two or four conductors to power and control the demultiplexer.

This technique of multiplexing/demultiplexing is already implemented in cardiology and neuromodulation applications.

In some cases, the demultiplexing circuit is located in the distal portion of the device, near the electrodes, being incorporated in the lead body. EP 1938861 A1, EP 2465425 A1 and US 2011/301665 A1 describe such arrangements. But it is noted that in these known constructions, the transverse dimensions of the lead body in its distal part are larger due to the need to tightly integrate the demultiplexing electronic circuit.

Alternatively, to avoid this difficulty, an intermediate component of quite large dimensions is provided midway between the generator and the lead tip (see in particular EP 2727623 A1), which complicates the implantation and creates a new risk because of the need to implement an additional element.

Moreover, the evolution of the conductor structures and of the lead electrode technology is such that it now becomes possible to produce leads with very small dimensions for stimulating and sensing electrical events in the heart.

Such structures may use conductors of a diameter of 40 to 60 µm and thus may include a plurality of conductors insulated from each other, typically, up to 100 separate conductors in a diameter less than 0.5 mm. It is not known to associate such structures to multiplexers without immediately meeting the above problems, in particular in terms of size, complexity and cost.

WO 2012/087370 A1 (corresponding to U.S. Pat. No. 8,639,341 B2) discloses an arrangement wherein the demultiplexing circuit is accommodated in a region of the connector body, with a support and connection block interposed between the multiplexed conductors and the non-multiplexed conductors. This block includes, in its center, an elongate support receiving the demultiplexing integrated circuit, where the circuit is electrically connected to the two respective groups of conductors coming from either side of the support. If this arrangement allows incorporating the demultiplexing methods to the connector, it has the disadvantage of a large footprint that significantly increases the length of the connector.

The present invention aims to overcome these limitations of the prior art and to propose a connection solution between a demultiplexer circuit and a multielectrode lead that is reliable and protected while being compact and which can be housed in the vicinity the lead connector, not requiring increase in diameter of the latter, and simplify the structure of the connections of the associated housing.

SUMMARY

The disclosure proposes for this purpose, in a first embodiment, a multielectrode lead including:

A connector for a control and/or power and/or data transfer connection;

A demultiplexing integrated circuit adapted to receive input on first conductors of the electrical control and/or power and/or data transfer signals from the control and/or power and/or data transfer link and connected at the output to a plurality of second conductors contained in the lead;

A gate circuit and connection element having a body forming a support for the demultiplexing integrated circuit and housed in a connector body bearing the connector and A set of electrodes extending along the lead and connected to the second conductors.

In some embodiments, the gate circuit and connection element:

Has a generally cylindrical form and receives the integrated circuit on one of its end sides;

Axially extending grooves;

Defines a set of connection cavities having the form of axially extending grooves in the periphery of the element body, with at least the second conductors distributed around a main axis of the body and disposed in the connection cavities; and Includes a set of connection elements embedded in the material of the body, emerging at a region of the element supporting the integrated circuit and at the respective cavities, these connection elements electrically connecting said first and/or second conductors to respective terminals of the integrated circuit.

According to various embodiments:

The conductor elements each have a protruding part extending in a respective groove on at least part of its axial length;

The conductive elements each have a first embedded portion generally extending axially and whose one end opens at a surface adjacent to the integrated circuit;

Each conductor element includes an intermediate embedded portion generally extending radially between the first embedded portion and the protruding portion extending in the groove;

The integrated circuit is protected by a cover tightly fixed on the body of the gate and connection circuit element;

The gate and connection circuit element is achieved by a ceramic-metal technology, the body of the element being constituted by a ceramic region and the connection elements being constituted by metal regions;

The gate and connection circuit element further includes a metal region for the cover welding;

The metal region is an annular region surrounding the integrated circuit;

The cover is also made of ceramic-metal technology and includes a counterpart metal region of the metal area surrounding the integrated circuit;

The conductors are surrounded at their free end, received in its respective cavity, by a metallic sleeve;

The lead further includes a transition element adapted to retain the second conductor in a configuration corresponding to the arrangement of the cavities for said second conductors;

The lead further includes a transition element adapted to retain the conductors in a first configuration corresponding to the arrangement of the cavities for said first conductors; and The body of the gate and connection circuit element includes at least two generally coaxial cylindrical portions of different diameters, each region having a plurality of axially extending grooves in its periphery.

In some embodiments, the disclosure provides a method for connection of conductors to a demultiplexing circuit in a localized stimulation multielectrode lead of the type described above, the method including the steps of:

a) mounting the integrated demultiplexing circuit on one of the end sides of the element;

b) connecting the circuit terminals to the emerging parts of the connection parts in the vicinity of the circuit; and c) connecting the conductors to the emerging parts of the connection regions at the cavities.

According to various other embodiments:

Step b) is implemented using connection wires;

Steps a) and b) are implemented simultaneously by a returned chip mounting technique;

Step c) is carried out by laser shots;

The conductors are surrounded at their free end, received in its respective cavity, by a metal sleeve;

The metallic material of the sleeve is the same as the metallic material of the gate and connection circuit element; and The method further includes steps of:

d) providing a cover at least partially made of metal to protect the integrated circuit;

e) providing the gate and connection circuit element a metal region surrounding the integrated circuit; and f) fixing the cover to said element by laser shots at the metallic region.

BRIEF DESCRIPTION OF THE DRAWINGS

Further features, characteristics and advantages of the present disclosure will become apparent to a person of ordinary skill in the art from the following detailed description of preferred embodiments of the present disclosure, made with reference to the drawings annexed, in which like reference characters refer to like elements and in which:

FIG. 1 and FIG. 1A are overall views in side elevation of a multielectrode lead with multiplexed control according to an embodiment of the disclosure.

FIG. 2 is a perspective view of a gate and connection circuit component of the lead of FIG. 1.

FIG. 3 is a perspective view of the component receiving a plurality of conductors for the electrodes and a protection cover of the circuit mounted on the component.

FIG. 4 is a side elevation view of the component of FIG. 2.

FIG. 5 is a front elevation view of the component of FIGS. 2 and 4.

FIG. 6 is an axial sectional view of a component having a different geometry from that of FIGS. 2 to 5, equipped with the circuit, the cover, the conductors and a protection jacket.

FIG. 7 is a front view of the representation of FIG. 6.

FIGS. 8 and 9 illustrate the assembly of FIGS. 6 and 7 of the component with its cover.

FIG. 10 shows in perspective view a layout of a conductor to be connected to the component.

FIG. 11 is a partial cross sectional view on an enlarged scale of the connection region between such a conductor and the component.

FIG. 12 is an exploded perspective view of a component with its cover, of conductors and transition parts for the conductors.

FIG. 13 is a perspective view of a variant of one of the two transition parts.

DETAILED DESCRIPTION

Figure 14:
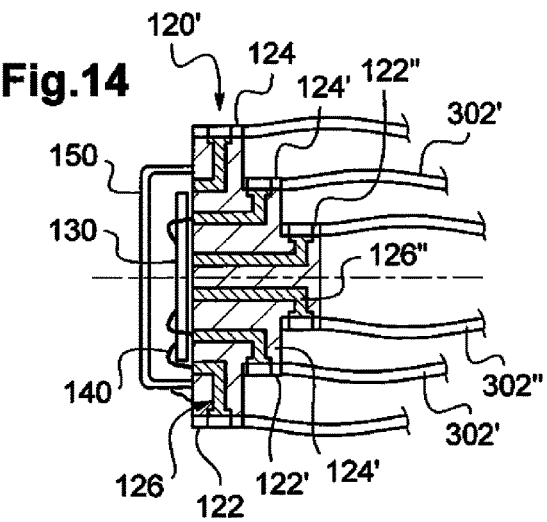
FIG. 14 is an axial sectional view of a variant embodiment of the component according to the disclosure equipped with the circuit, the cover and the conductors.

Referring firstly to FIGS. 1 and 1A, an integrated demultiplexing multielectrode lead is shown. The lead includes a tapered intermediate body 100 housing a gate and connection circuit component 120 as is described below, and a connector 110 with a control and/or supply and/or data transfer connection 200, typically with two or four conductors. The lead 300 houses a plurality of conductors 302, typically from eight pairs of conductors to several tens of pairs of conductors, these conductors being connected to a set of stimulation electrodes 306 spaced along the lead.

In the example illustrated in FIGS. 1 and 1A the link 200 with 2 (or 4) conductors is a connection incorporated to the connector 110, and connected to the 2 (or 4) poles 200a, 200b of the connector. This is a particularly advantageous embodiment, since it is able to include the multiplexer stage within the connector, thus without additional congestion, in particular in the diametric dimension.

However, it must be kept in mind that the disclosure can be applied to many other configurations; each time it is necessary to interface a device with a detection/stimulation multielectrode lead by a multiplexer/demultiplexer stage. The device in question may in particular be any type of neurostimulator, or pacemaker, and in particular be in a stand-alone device with its own power supply (leadless implantable capsule) and extended by a multielectrode lead which it is connected by a communication system, etc.

Advantageously, but not limiting, the connector 110 is in the illustrated example a standard connector of the IS-1 type (to which two conductors 202 accommodated in the body 100 are connected, according to the shown example) or of the IS-4 type (four conductors). The lead 300 has in the present example ten conductors 302 and two conductors 202.

Referring now to FIGS. 2 to 5, a component 120 housed within the body 100 is illustrated, whose main functions are to receive an electronic demultiplexing circuit responsive to the signals coming through the conductors 202, connected to the link 200 by the connector 110, for selectively applying stimulating pulses to one of the electrodes 306 (or to a given subset of said electrodes).

This component includes a generally cylindrical main body defined by a cylindrical outer wall 122 in which a series of longitudinal grooves 124 are formed, intended, as discussed in the following, to make a connection with the conductors of the link 200 and the conductors of the lead part 300. In this embodiment, the grooves 124 are twelve in number: two for the conductors 202, departing in the direction of the link 200, and ten for conductors 302, departing towards the lead part 300.

On one of its end faces, here on its proximal face, the component 120 receives an integrated circuit 130 for providing the function of demultiplexing the signals received via the connection 200 for controlling the pulses as described above.

This integrated circuit includes at its surface (or, alternatively (not shown), at its sides), conductive pads or areas 132 allowing the integrated circuit to be connected to its environment by connection wires (bonding wires) 140. In the component body a plurality of conductive elements 126a-126c intended to ensure the connection between the circuit 130 and the conductors of the connecting part 200 and the lead 300 are embedded, as will be described in detail later.

FIG. 3 illustrates a cover 150 to be fixed tightly on the face of the component 120 receiving the circuit 130, as will be described hereinafter, so as to protect the circuit 130 and the bonding wires.

Referring to FIGS. 6 to 9 which illustrate a component having a slightly different geometry from that of FIGS. 2 to 5 (mostly with a shorter axial length), the configuration of the inner conductor elements 126a-126c of the component 120 can be seen.

Each element includes a first part 126a extending axially flush at its free end on the side of the component body 120 which carries the circuit 130, by opening the periphery of the circuit. This first part is extended by a portion 126b oriented generally radially, towards one of the longitudinal grooves 124, each for receiving a conductor 202 or 303. This portion 126b terminates in a portion 126c which opens into the groove 124 extending over at least part of its axial extent.

The electrical connection between the multiplexing circuit 130 and each of the conductors is carried out, circuit 130 side, by the bonding wire 140 welded on the one hand on the conductive pads 132 of the circuit and the other hand on the flush regions of the portions 126a of the embedded conductive elements, respectively. The connection of conductors' side 202, 302 is carried out as will be seen in detail below by contacting exposed portions of the conductors with the portions 126c of the conductive elements which open into the respective grooves 124.

According to an alternative embodiment not illustrated, the electrical connection between the conductive pads of the circuit 130 and the respective conductive elements 126a-126c may be performed according to known technology called "flip-chip", the chip having slightly protruding contacts on its face turned towards the component 120 and these contacts being connected to flush areas of the portions 126a of conductive elements 126a-126c. This technique avoids the use of bonding wires.

Advantageously, the component body 120 and its conductive members 126a-126c are made of "cermet", that is to say, a composite material with metal matrix including a ceramic reinforcement, for example of alumina/platinum, the main, insulating, part of the body being made of ceramic (here alumina) and the conductive elements 126a-126c being made of platinum. Alternatively, one may use a composite of type alumina/tungsten-molybdenum. One can also use a ceramic of the type silicon carbide.

The manufacturing methods of such elements, which are the advantage of a continuous transition between the insulating part and the conductive part are largely controlled and make it possible to manufacture a component with a design adapted to this application (sizing of the various parts of the device will be discussed below).

Furthermore, the component 120 produced in this way allows, in cooperation with a cover 150 as will be described in detail below, to hermetic seal the cavity housing the integrated circuit 130, which may be difficult to obtain by molding a synthetic material injected on the metallic conductors.

Referring to FIGS. 8 and 9, the cover 150 of the protection circuit 130 is incorporated and fixed tightly on the face of the component 120 which carries the integrated circuit 130, as illustrated.

The cover is also realized here in cermet technology and includes an insulating main body forming a cavity 154 intended to house the circuit 130 and a conductive annular region 152 facing the component 120. In association with this cover, on component 120 a further conductive area 128 of generally annular shape, by example same geometry as the annular area 152 of the cover, flush with the surface that carries the circuit 130, is arranged around the latter. Note that the cermet technology for manufacturing of the component 120 makes it easy to integrate such an annular conductive region.

With such a configuration, once the bonding wires 140 are connected, the cover 150 is applied and maintained against the face of the component 120 on the circuit 130 and a welding point by point laser shots is then implemented in a plurality of places at the junction between the annular zones 128, 152, the weld points being designated in FIG. 9 by reference 170. This method ensures a completely sealed connection between the component 120 and the cover 150, to thereby perfectly protect the circuit 130 and its connections.

Note here that the principle of closure of the cavity housing the circuit 130 makes it possible to minimize excessive elevation of the temperature within the cavity, which can be maintained below 400° C.

It will also be noted here that the configuration of FIGS. 2 and 3 is slightly different from that of FIGS. 5 to 9. In FIGS. 2 and 4, the conductive area for the sealed welding of the cover 150 is designated by reference 129. It extends not in a general radial plane but according to a circumferential cylinder at an area of reduced diameter adjacent to its face supporting the circuit 130, of component 120.

Finally, according to an embodiment, the welded cover 150 may be made entirely of biocompatible metal, such as titanium alloy.

According to another embodiment, the cover can be fixed tightly on the component 120 by bonding.

In all cases, it may be advantageous to further strengthen the protection of the circuit and of its associated connections by encapsulating the assembly formed by the component 120 and its cover 150, housing the circuit 130, and the connected wires, in a block of flexible polymer 160, for example of silicone, this block also enclosing a short length of the conductors 202, 302 to mechanically secure the assembly.

Referring now to FIGS. 10 and 11, it is described in detail a method in which the conductors 202, 302 are mechanically held and electrically connected to the component 120, at respective grooves 124. Advantageously, and as illustrated in FIG. 10, such a conductor, here a conductor 302 located electrodes side, receives at one end portion 302a stripped of its insulating sheath 302b, a hypotube 304 to facilitate the connection method. This hypotube, here made of platinum, may be welded to conductor 302 by laser shot, or simply threaded thereon during assembly.

As shown in FIG. 11, the end of the conductor provided with the hypotube 304 is positioned and held in line with a groove 124 corresponding to a final destination. It is noted that the conductive portion 126c opening into the groove 124 forms a semi-cylindrical cavity having a diameter close to the outside diameter of the hypotube 304 such that it is intimately housed there.

Then a laser shot (or several shots, on each side) is performed at the transition between the hypotube 304 and the conductive portion 126c, on each side, to provide mechanical attachment and electrical connection of the group consisting of the core 302a of the conductor and the hypotube 304 with the conductive part 126c of the conductive element 126a-126c, which is connected at the opposite end to the integrated circuit 130.

Note here that the hypotube 304 may reduce the risk of poor connection during the laser shot. It may be omitted in the case wherein the reliability of the laser firing method is sufficient, in which case the conductive core 302a of the conductor 302 is directly welded to the part 126c of the conductive element 126a-126c (and similarly for the conductors 202).

According to a non-illustrated embodiment, the electrical connection between the component 120 and the conductors 202, 302 may be performed without use of laser shot welding. More specifically, by placing the conductors 202, 302 into their respective groove 124 and applying around the entire assembly strapping, for example by use of a PEEK ring (polyether-ether-ketone) which crimps the conductors 202, 302 against their respective conductive parts 126c. A slight taper from the periphery of the component 122 may be provided to perform this function, the ring being moved to the portion of larger outside diameter of the component, and then bonded.

Referring now to FIG. 12, advantageously, transition parts, respectively 400, 500, are associated with the gate and connection circuit component 120 to ensure a prepositioning of the conductors 202, 302 to connect the component, respectively.

Thus, the part 400, made of injected synthetic material, has the shape of a cylinder with an outer diameter close to that of component 120, and has in diametrically opposite regions two through holes 402 generally parallel in the axial direction, the distance between these orifices being approximately the distance between two diametrically opposed grooves 124 of the component. The two conductors 202 are threaded through two holes and then engaged in their respective groove 124, the part 400 ensuring prepositioning of both conductors during the soldering or crimping operations.

In the same spirit, a part 500, also of injected synthetic material, here includes ten through holes 502 generally parallel to the axial direction, in which the ten conductors 302 are threaded before being put in place in their respective groove. This transition part 500 is generally cylindrical, here.

It is understood that these transition parts can be particularly useful, especially at the side of the main portion 300 of the lead, when a large number of conductors are to be positioned on the component 120.

After soldering or crimping of conductor, parts 400, 500, for example bonded to both sides of the component 120 with its cover 150, ensure dimensional stability of the assembly and prevent the conductors from being accidentally folded and optionally cut during handling.

As shown in FIG. 13, we can give the transition part 500 a generally conical shape, the orifices 502 converging from an area adjacent to the component 120, where they adopt an arrangement corresponding to that of counterpart grooves, in direction of a distal narrowed area where all conductors 302 join in the portion of the lead 300.

Figure 15:
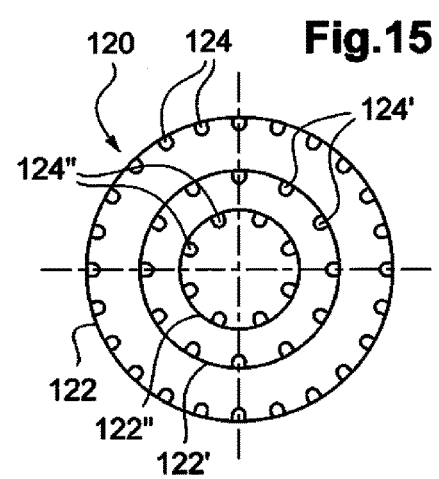
FIG. 15 is a back view of the equipped component of FIG. 14.

We will now describe with reference to FIGS. 14 and 15 an alternative embodiment of the gate and connection circuit component, allowing the connection of an increased number of conductors 302.

In this embodiment, the gate and connection circuit component designated by the reference 120' comprises three cylindrical stages for peripheral connections with conductors, coaxial and of progressively decreasing diameter as the distance increases from the part supporting the integrated circuit 130.

Thus, FIGS. 14 and 15 illustrate a first set of grooves 124 made in the region of the widest stage, a second set of grooves 124' formed through the following stage, of intermediate diameter, and a third set of grooves 124" performed at the top stage of smaller diameter.

The component 120 houses three groups of embedded conductive elements, respectively 126, 126' and 126", whose configurations are adapted to the geometry of the component body to provide each a flush connection surface, these connecting surfaces being distributed around the circuit.

The cylindrical peripheries of the three stages are designated by references 122, 122' and 122".

It is understood that such a configuration may significantly increase the connection density. Typically it becomes possible to connect up to a hundred or more conductors 302, to make leads provided with very many electrodes, providing excellent opportunities for stimulation location.

Advantageously, the component 120' according to this embodiment is also manufactured according to the cermet technology, and the transition part 500, if such a part is provided, is adapted accordingly.

The disclosure enables a multielectrode lead with microconductors, of a typical diameter of 0.3 mm with current technology, with an intermediate portion dedicated to both the connection to a connector (e.g. a standard connector of IS-1 or IS-4 type) and to demultiplexing, whose diameter does not exceed 3 to 4 mm (with a chip having a size of 1 mm$^2$, which can be achieved with the current integration of performance).

The present disclosure has many advantages, including the following:

It makes possible the integration of the demultiplexing in the lead, while keeping it a small diameter, typically of the order of 0.3 mm in the current technology, with a gradual transition between the housing for the demultiplexing circuit and the lead itself;

It is compatible with a standard connector (e.g. type a 2 wire IS-1 connector or a 4 wire IS-4 connector) and allows miniaturization of the region dedicated to the demultiplexing of the signals arriving at these connectors;

Manufacture may be economical, with welds by a laser shooting robot on components whose cost can remain reasonable;

It can significantly increase the number of connections (100 connections or more) while maintaining a reasonable size for the demultiplexing part;

It ensures a tightness and protection of the area housing the demultiplexing integrated circuit through hermetically fixing the cover and optionally the encapsulation in a soft polymer; and It enables very short electrical connections, with low risk of incorrect connections due to conductor breaks.

Figure 16:
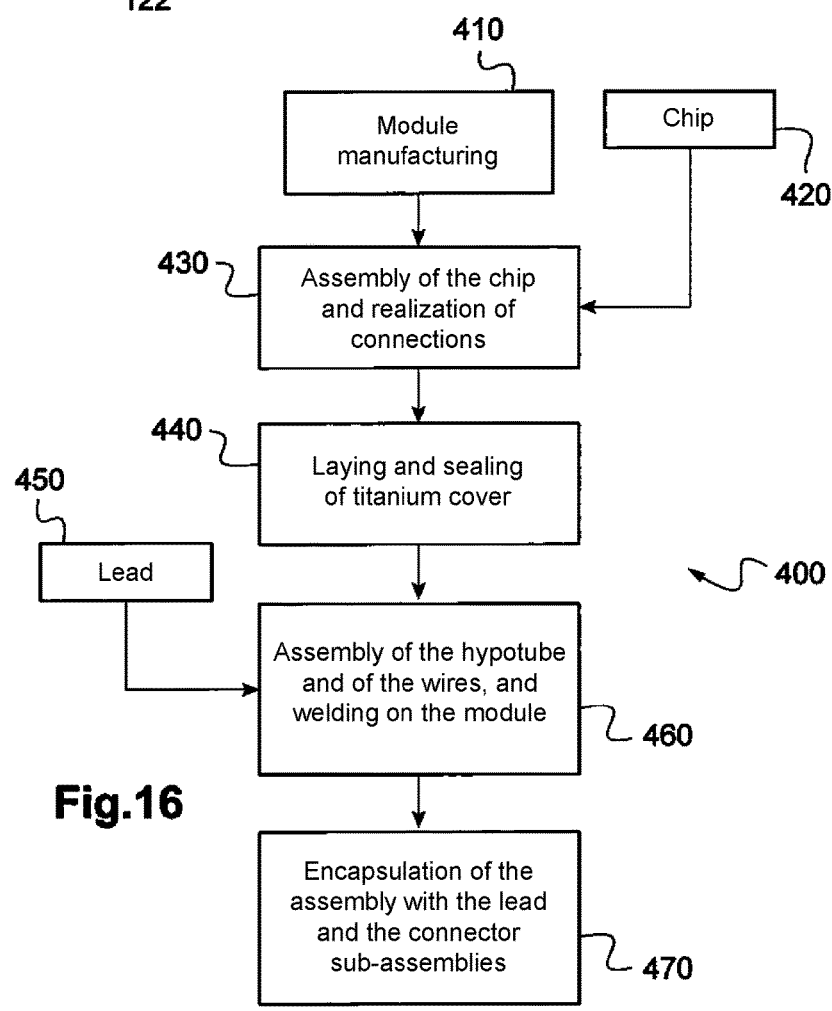
FIG. 16 schematically illustrates the successive steps of mounting a multielectrode lead carried out according to the teachings of the disclosure.

As regards more particularly the manufacturing method of a multielectrode lead formed according to the teachings of the present disclosure, it can be summarized schematically to the steps shown in the flowchart 400 of FIG. 16, namely:

Component 120 manufacturing (step 410);

In parallel, preparation of the integrated circuit chip 130 (step 420);

Mounting the chip 130 on the component 120 and realization of connection bonding 140 (step 430);

Laying and sealing of titanium cover 150 on the component 120 (step 440);

Preparation of the lead (step 450), then mounting of the hypotube 304 and placement and welding of the conductors 202, 302 on the component (step 460); and Finally, encapsulation of the assembly with the lead and the various subassemblies of the connector 110 (step 470).

What is claimed is:

1. A multielectrode lead for localized stimulation, comprising:
    a connector;
    a circuit configured to input, from a plurality of first conductors, signals from the connector, the circuit connected to a plurality of second conductors contained in the lead;
    a circuit component housed within a lead body, the circuit component carrying the connecter and configured to support the circuit; and
    a plurality of electrodes connected to the second conductors,
    wherein the circuit component:
        is cylindrical and houses the circuit;
        comprises a plurality of longitudinal grooves extending around a periphery of the circuit component, wherein at least the second conductors are disposed within the plurality of grooves; and
        comprises a plurality of conductive elements embedded in the body of the circuit component, wherein the conductive elements electrically connect the first and second conductors to respective terminals of the circuit.

2. The lead of claim 1, wherein each of the conductive elements have a protruding contact extending in a respective groove along at least part of its axial length.

3. The lead of claim 1, wherein the conductive elements each have a first embedded portion extending axially and opening at one end on a surface adjacent to the circuit.

4. The lead of claim 3, wherein each conductive element comprises an intermediate embedded portion generally extending radially between the first embedded portion and the protruding contact extending in the groove.

5. The lead of claim 1, wherein the circuit is protected by a cover sealingly fixed to the body of the circuit component.

6. The lead of claim 5, wherein the circuit component further comprises a metal region to which the cover is welded.

7. The lead of claim 6, wherein the metal region is an annular region surrounding the circuit.

8. The lead of claim 6, wherein the cover is made of metal-ceramic technology and comprises a homologous metal region of the metal region surrounding the circuit.

9. The lead of claim 1, wherein the circuit component is formed by a metal-ceramic technology, the body of the circuit component comprising a ceramic region and the conductive elements comprising a plurality of metal regions.

10. The lead of claim 1, further comprising a transition member adapted to retain the second conductors in a configuration corresponding to the arrangement of the grooves for the second conductors.

11. The lead of claim 1, wherein the body of the circuit component comprises at least two cylindrical regions, generally coaxial and of different diameters.

12. An implantable medical device, comprising:
a stimulation pulse generator; and
a multielectrode lead for localized stimulation, comprising:
   a connector;
   a circuit configured to input, from a plurality of first conductors, signals from the connector, the circuit connected to a plurality of second conductors contained in the lead;
      a circuit component housed within a lead body, the circuit component carrying the connecter and configured to support the circuit; and
   a plurality of electrodes connected to the second conductors,
   wherein the circuit component:
      is cylindrical and houses the circuit;
      comprises a plurality of longitudinal grooves extending around a periphery of the circuit component, wherein at least the second conductors are disposed within the plurality of grooves; and
      comprises a plurality of conductive elements embedded in the body of the circuit component, wherein the conductive elements electrically connect the first and/or second conductors to respective terminals of the circuit.

13. The implantable medical device of claim 12, wherein the device is a pacemaker or a neurostimulator.

14. The implantable medical device of claim 12, wherein each of the conductive elements have a protruding contact extending in a respective groove along at least part of its axial length.

15. The implantable medical device of claim 12, wherein the conductive elements each have a first embedded portion extending axially and opening at one end on a surface adjacent to the circuit.

16. The implantable medical device of claim 15, wherein each conductive element comprises an intermediate embedded portion generally extending radially between the first embedded portion and the protruding contact extending in the groove.

17. The implantable medical device of claim 12, wherein the circuit is protected by a cover sealingly fixed to the body of the circuit component.

18. The implantable medical device of claim 17, wherein the circuit component further comprises a metal region to which the cover is welded.

19. The implantable medical device of claim 18, wherein the metal region is an annular region surrounding the circuit.

20. The implantable medical device of claim 18, wherein the cover is made of metal-ceramic technology and comprises a homologous metal region of the metal region surrounding the circuit.

* * * * *